United States Patent
Ahmed et al.

(10) Patent No.: US 11,833,246 B1
(45) Date of Patent: Dec. 5, 2023

(54) RECTAL GEL WITH DATE PALM PHENOLICS AND VANILLIC ACID

(71) Applicant: KING FAISAL UNIVERSITY, Al-Ahsa (SA)

(72) Inventors: Hany Ezzat Khalil Ahmed, Al-Ahsa (SA); Hairul Islam Mohamed Ibrahim, Al-Ahsa (SA); Krishnaraj Thirugnanasambantham, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/218,438

(22) Filed: Jul. 5, 2023

Related U.S. Application Data

(62) Division of application No. 18/113,721, filed on Feb. 24, 2023.

(51) Int. Cl.

| | |
|---|---|
| *A61K 9/06* | (2006.01) |
| *A61K 47/46* | (2006.01) |
| *A61K 31/515* | (2006.01) |
| *A61K 47/42* | (2017.01) |
| *A61K 47/38* | (2006.01) |
| *A61K 47/12* | (2006.01) |
| *A61K 31/5513* | (2006.01) |
| *A61P 1/00* | (2006.01) |

(52) U.S. Cl.
CPC ............. *A61K 9/06* (2013.01); *A61K 31/515* (2013.01); *A61K 31/5513* (2013.01); *A61K 47/12* (2013.01); *A61K 47/38* (2013.01); *A61K 47/42* (2013.01); *A61K 47/46* (2013.01); *A61P 1/00* (2018.01)

(58) Field of Classification Search
CPC .... A61K 9/06; A61K 31/515; A61K 31/5513; A61K 47/12; A61K 47/38; A61K 47/42; A61K 47/46; A61P 1/00
USPC .......................................................... 514/221
See application file for complete search history.

(56) References Cited

U.S. PATENT DOCUMENTS

2022/0105200 A1    4/2022   Liechty

FOREIGN PATENT DOCUMENTS

| CN | 102108138 A | 6/2011 |
| CN | 106893004 A | 6/2017 |
| CN | 108465123   | 8/2018 |

(Continued)

OTHER PUBLICATIONS

S.S. Al Harthi et al., "Quantification of phenolic compounds, evaluation of physicochemical properties and antioxidant activity of four date (*Phoenix dactylifera* L.) varieties of Oman," Journal of Taibah University Medical Sciences, 10(3), (2015).

(Continued)

*Primary Examiner* — Taylor V Oh
(74) *Attorney, Agent, or Firm* — Nath, Goldberg & Meyer; Richard C. Litman

(57) ABSTRACT

A gel composition for treating bowel diseases comprising about 0.1 to about 2.5 wt. % of an anti-epileptic agent; about 0.8 to about 2.0% wt. % of a collagen complexed with a date palm extract of Khalas cultivar and carboxymethylcellulose; about 10 to about 50 µg/mL of vanillic acid; about 0.1 to about 0.3 µg of stearic acid; and water; wherein all wt. % are based on g/100 g of the gel composition. This gel composition can be topically administered to the rectum of a patient to treat one or more bowel diseases, disorders, or conditions.

12 Claims, 3 Drawing Sheets

(56) References Cited

FOREIGN PATENT DOCUMENTS

| | | |
|---|---|---|
| CN | 113519736 A | 10/2021 |
| EP | 2380564 A2 | 10/2011 |
| WO | 2021252885 A1 | 12/2021 |

OTHER PUBLICATIONS

Li, Manman et al., "Oligoarginine mediated collagen/chitosan gel composite for cutaneous wound healing," Int. J. Biol. Macro. (2018).

Jhoodoo et al., "Anti-Inflammatory Activity of Chitosan and 5-Amino Salicylic Acid Combinations in Experimental Colitis," Pharmaceutics. 12(11) (2020).

RECTAL GEL WITH DATE PALM PHENOLICS AND VANILLIC ACID

CROSS-REFERENCE TO RELATED APPLICATION

This application is a divisional of U.S. patent application Ser. No. 18/113,721, filed on Feb. 24, 2023.

BACKGROUND

1. Field

The disclosure of the present patent application relates to a gel composition for treating bowel diseases.

2. Description of the Related Art

Patients diagnosed with various forms of bowel irritation, worldwide, have drastically increased over the last decade. These chronic conditions can result in significant morbidity for individuals including long hospitalizations, prolonged exposure to antibiotics, acute and chronic pain, the need for cumbersome wound care, and restricted mobility. Despite the enormous impact of these chronic wounds on both individuals and society, effective therapies are lacking. Thus, the modification, correction, or prevention of such bowel irritation has far-reaching consequences, both on patient outcomes and on healthcare expenditures.

For example, inflammatory bowel disease (IBD), specifically ulcerative colitis, is characterized by intestinal inflammation, oxidative stress, and a disrupted mucosal barrier. Because current treatments are largely inefficient to improve symptoms and survival of patients suffering from IBD, such as ulcerative colitis, alternative therapies are urgently needed.

One product being studied for its use in wound healing is collagen, which may promote healing by restoring or preventing the breakdown of the skin or tissue/organ extracellular matrix. Collagen is a biodegradable protein and exists in a form of fibers in connective tissue of most animals. The primary function of collagen is to maintain the integrity of tissues and to provide tensile strength essential to tissues. At present, more than 21 different types of collagen have been discovered.

Collagen can be manufactured in different forms, such as sponge, gel, tube, or sheet. A porous collagen matrix can facilitate cell migration, cell growth or encapsulation and release of drugs. Processes for the preparation of a collagen matrix typically include comminuting starting materials generally by slicing or grinding, extraction, purification, lyophilization, and further comprising a cross-linking process. Acidic or alkaline collagens are generally used and cross-linked by a dehydrothermal process or by some chemical cross-linking agents and lyophilized to obtain porous collagen matrices.

Further, although there are numerous products for bowel irritation on the market, many consumers are hesitant to use chemically synthesized products perceived as being environmentally unfriendly or otherwise unsafe. Consequently, there is a need for such products that are effective and have natural components. Thus, a bowel treating composition solving the aforementioned problems is desired.

SUMMARY

The present subject matter relates to a gel composition for treating bowel diseases in a patient.

In one embodiment, the present subject matter relates to a gel composition comprising: about 0.1 to about 2.5 wt. % of an anti-epileptic agent; about 0.8 to about 2.0% wt. % of a collagen complexed with a date palm extract of Khalas cultivar and carboxymethylcellulose; about 10 to about 50 µg/mL of vanillic acid; about 0.1 to about 0.3 µg of stearic acid; and water; wherein all wt. % are based on g/100 g of the gel composition.

In another embodiment, the present subject matter relates to a method for treating a bowel disease, disorder, or condition in a patient in need thereof, the method comprising: topically administering a therapeutically effective amount of the gel composition as described herein to a rectum of the patient.

The present subject matter also relates to the use of a gel composition as described herein in the manufacture of a medicament for treating a bowel disease, disorder, or condition in a patient.

The present subject matter further relates to a pharmaceutical formulation comprising the gel composition as described herein for treating, reducing the risk of, preventing, or alleviating a symptom of a bowel disease, disorder, or condition in a patient.

In some embodiments of the present subject matter, the gel composition is administered topically, intradermally, or intramuscularly to the patient. In some embodiments, the gel composition is administered rectally to the patient. In some embodiment, the gel composition is administered to the patient a plurality of times. In some examples, the composition is administered rectally to the patient. In some embodiment, the gel is administered daily to the patient.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Detailed Description and no limitation as to the scope of the present disclosure is intended by either the inclusion or non-inclusion of elements, components, etc. in this Summary.

These and other features of the present subject matter will become readily apparent upon further review of the following specification.

DETAILED DESCRIPTION OF THE PREFERRED EMBODIMENTS

Figure 1:
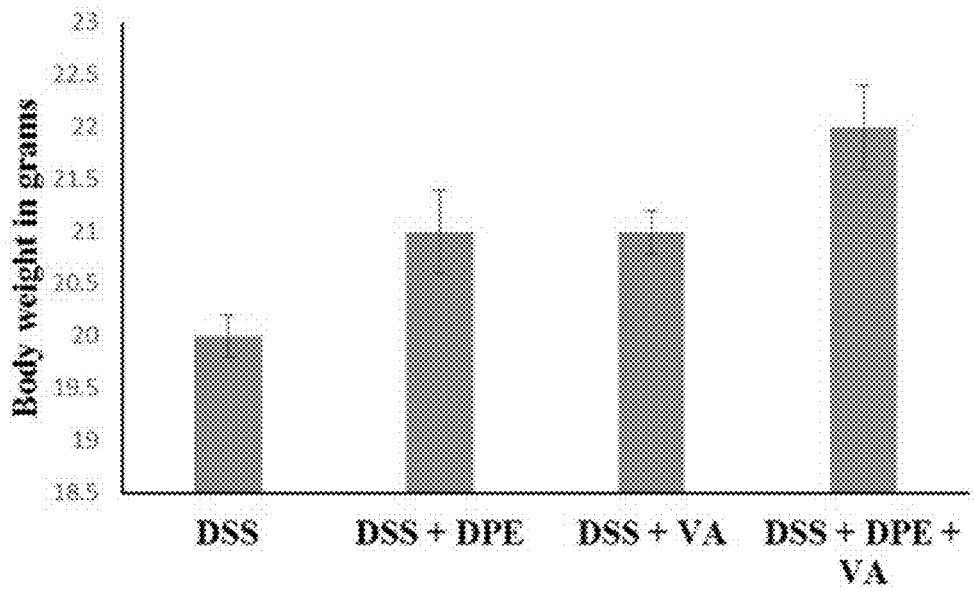
FIG. 1 is a chart various dosages of different compositions based on patient body weight.

The following definitions are provided for the purpose of understanding the present subject matter and for construing the appended patent claims.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

A "subject" herein is typically a human. In certain embodiments, a subject is a non-human mammal. Exemplary non-human mammals include laboratory, domestic, pet, sport, and stock animals, e.g., mice, cats, dogs, horses, and cows. Typically, the subject is eligible for treatment, e.g., treatment of a gastrointestinal inflammatory disorder. As used herein, the term "patient" refers to any single subject for which treatment is desired. In certain embodiments, the patient herein is a human. A subject can be considered to be in need of treatment.

As used herein, "gastrointestinal inflammatory disorders" or "bowel diseases, disorders, or conditions" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis Inflammatory Bowel Disease (IBD) is used interchangeably herein to refer to diseases of the bowel that cause inflammation and/or ulceration and includes without limitation Crohn's disease and ulcerative colitis. Crohn's disease (CD) and ulcerative colitis (UC) are chronic inflammatory bowel diseases of unknown etiology. Crohn's disease, unlike ulcerative colitis, can affect any part of the bowel. The most prominent feature of Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

Ulcerative colitis (UC) afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus, and mucus with scanty fecal particles. A total colectomy may be required for acute, severe or chronic, unremitting ulcerative colitis. The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

An "effective amount" of a gel composition as described herein is an amount sufficient to carry out a specifically stated purpose. An "effective amount" may be determined empirically and in a routine manner, in relation to the stated purpose. The term "therapeutically effective amount" refers to an amount of a gel composition as described herein to "treat" a disease or disorder in a subject.

As used herein, "suppressing", "suppress", or "suppression" means stopping the inflammation from occurring, worsening, persisting, lasting, or recurring.

"Reducing", "reduce", or "reduction" means decreasing the severity, frequency, or length of one or more symptoms of a disease, disorder, or condition as described herein.

"Treating" or "treatment" or "alleviation" refers to both therapeutic treatment and prophylactic or preventative measures, wherein the object is to prevent or slow down (lessen) the targeted pathologic disease, condition, or disorder. Those in need of treatment include those already with the disease, condition, or disorder as well as those prone to have the disease, condition, or disorder or those in whom the disease, condition, or disorder is to be prevented. A subject or mammal is successfully "treated" for a disease, condition, or disorder if, after receiving a therapeutic amount of a gel composition as described herein, the subject shows observable and/or measurable reduction in, or absence of, one or more symptoms of the disease, condition, or disorder. Reduction of these signs or symptoms may also be felt by the patient.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter is directed to a gel composition for treating bowel diseases in a patient. In one embodiment, the present subject matter relates to a gel composition comprising: about 0.1 to about 2.5 wt. % of an anti-epileptic agent; about 0.8 to about 2.0% wt. % of a collagen complexed with a date palm extract of Khalas cultivar and carboxymethylcellulose; about 10 to about 50 µg/mL of vanillic acid; about 0.1 to about 0.3 µg of stearic acid; and water; wherein all wt. % are based on g/100 g of the gel composition.

In certain embodiments, the gel composition can further comprise one or more components selected from the group consisting of chitosan, timogen, propylene glycol, Carbopol, EDTA, and sodium hydroxide. In this regard, 0.01-1.0 mM sodium hydroxide can increase the gelling rheology. The timogen and chitosan can improve the absorption of active moieties in the gel and lead to decreased disease symptoms and treatment period.

In an embodiment, the collagen used in the present gel compositions contains one or more collagen enzymatic hydrolysates. By way of non-limiting example, the collagen used in the present gel compositions is pepsin treated collagen I, which can undergo gelatinization followed by enzymatic hydrolysis. The collagen used can be obtained from connective tissue of any suitable animal, e.g., cow, pig, sheep, chicken, duck, turkey, goose, whale, or shark. The connective tissue can include skin, dermis, subcutaneous tissue, ligament, tendon, aponeurosis, cartilage, bone tissue, cornea, sclera, aorta, vessel, and the like.

In certain embodiments, the collagen used in the present gel compositions can be made by heating a collagen hydrolysates solution, adjusting the pH of the solution, and adding papain to perform enzymolysis to obtain an enzymolysis reaction solution. In this regard, collagen undergoing this process and being used in the present gel compositions can be dosed in an amount of about 5 to about 15 mg/kg body weight of the patient, or about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, or any range of any two endpoints thereof, by body weight of the patient. Further such collagen can include about 25 to about 80 mg/kg body weight of the patient, of collagen enzymatic hydrolysates, or about 25 mg/kg, about mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, or any range of any two endpoints thereof, by body weight of the patient, of collagen enzymatic hydrolysates.

In another embodiment, the date palm extract used in the present compositions is an extract of the Khalas cultivar date palm. The vanillic acid is one phenolic component of the date palm extract from the Khalas cultivar date palm. As the concentration of vanillic acid in the date palm extract is less than other phenolic components of the date palm extract, it may be necessary to add vanillic acid obtained from an outside source to provide an effective amount of vanillic acid. In certain embodiments, an effective amount of vanillic acid in the present composition is about 10 µg/mL to about 50 µg/mL of vanillic acid, or about 10 µg/mL, about µg/mL, about 20 µg/mL, about 25 µg/mL, about 30 µg/mL, about 35 µg/mL, about 40 µg/mL, about 45 µg/mL, about 50 µg/mL, or any range of any two endpoints thereof, of vanillic acid. The date palm extract may contain other phenolic components, by way of non-limiting example including gallic acid, p-coumaric acid, caffeic acid, vanillic acid and syringic acid. In certain embodiments, it is anticipated the presence of the vanillic acid in the designated amounts in the present gel compositions will contribute to enhancing healing properties of the gel compositions.

The total phenolic content of the date palm extract used can be determined by a modified Folin-Ciocalteu method, wherein 1 mg of the date palm extract is suspended in 1 ml water, with 100 µl of Folin—Ciocalteu reagent being added to the mixture after 1 minute. Subsequently, the mixture is incubated in a shaking incubator at 40° C. for 30 min and its absorbance measured at 760 nm. Gallic acid can be used as a standard for the calibration curve. The phenolic content can be expressed as gallic acid equivalents by using the following linear equation: $y=0.921x+0.0227$, $R^2=0.9771$, where y is the absorbance and x is the concentration as gallic acid equivalents (mg/ml). Following this procedure, the estimated quantity of total phenolic content in the date palm extract was 22.86 mg gallic acid equivalents/g of dry date palm extract. Accordingly, the present gel compositions can contain about 20 to about 25 mg of total phenolics per g of dry date palm extract, or about 20 mg, about 20.5 mg, about 21 mg, about 21.5 mg, about 22 mg, about 22.5 mg, about 23 mg, about 23.5 mg, about 24 mg, about 24.5 mg, about 25 mg, or any range of any two endpoints thereof, of total phenolics per g of dry date palm extract.

The present compositions can further comprise carboxymethylcellulose and stearic acid, in addition to water as a carrier. In certain embodiments, the combination of collagen containing the date palm extract when complexed with the carboxymethyl cellulose will be present in the instant gel compositions in an amount of about 0.8 to about 2.0 wt. % by weight of the total gel composition, or about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, or any range of any two endpoints thereof, of this combination. Similarly, in certain embodiments, the stearic acid will be present in the instant gel compositions in an amount of about 0.1 to about 0.3 µg, or about 0.1 µg, about 0.2 µg, about 0.3 µg, or any range of any two endpoints thereof, of stearic acid.

The present compositions can further comprise an anti-epileptic agent. In this regard, the present gel compositions can include about 0.1 to about 2.5 wt. % of an anti-epileptic agent, or about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, or any range of any two endpoints thereof, of the anti-epileptic agent, on a wt. % basis with respect to 100 g of the gel compositions. In other embodiments, the present gel compositions can include-about 0.25 to about 1.5 wt. % of the anti-epileptic agent, or about 0.75 wt. % of the anti-epileptic agent.

In certain embodiments, the anti-epileptic agent can be a phenobarbital. In further embodiments, the phenobarbital can be diazepam. Other anti-epileptic agents, phenobarbitals, and the like are further contemplated for use herein. By way of non-limiting example, certain anti-epileptic agents that can be used in the present gel compositions can include Brivaracetam (Briviact), Carbamazepine (Tegretol), Clobazam (Frisium), Clonazepam (Rivotril), Diazepam (Valium), Ethosuximide (Zarontin), Gabapentin (Neurontin), Lacosamide (Vimpat), Lamotrigine (Lamictal), Levetiracetam (Keppra), Midazolam, Oxcarbazepine (Trileptal), Perampanel (Fycompa), Phenobarbitone (Phenobarb), Phenytoin (Dilantin), Pregabalin (Lyrica), Primidone (Mysoline), Rufinamide (Inovelon), Sodium valproate (Epilim, Valpro), Tiagabine (Gabitril), Topiramate (Topamax), Vigabatrin (Sabril), and Zonisamide (Zonegran).

The present gel compositions may further includeone or more "pharmaceutically-acceptable excipients" or "pharmaceutically-acceptable carriers" means a pharmaceutically acceptable material, composition, or vehicle involved in giving form or consistency to the gel composition. Each excipient or carrier must be compatible with the other ingredients of the pharmaceutical composition when comingled such that interactions which would substantially reduce the efficacy of the active gel compositions of this disclosure when administered to a subject and interactions which would result in pharmaceutical compositions that are not pharmaceutically acceptable are avoided. In addition, each excipient or carrier must of course be of sufficiently high purity to render it pharmaceutically-acceptable. Suitable pharmaceutically acceptable excipients may include diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the gel-based formulations of this disclosure. In addition, there are resources available to the skilled artisan which describe pharmaceutically-acceptable excipients and may be useful in selecting suitable excipients for use in the gel-based compositions of this disclosure. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press), the contents of each of which may be incorporated herein in their entirety.

Therapeutic formulations comprising the gel compositions of this disclosure may be prepared for storage by mixing the gel composition having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations.

Sustained-release preparations may be prepared. Suitable examples of sustained-release preparations may include semipermeable matrices of solid hydrophobic polymers containing the gel compositions of this disclosure in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(—)-3-hydroxybutyric acid. While polymers such as ethylene-vinyl acetate and lactic acid-glycolic acid enable release of molecules for over 100 days.

Thus, one aspect of this disclosure is a therapeutic formulation comprising the gel composition of this disclosure adapted for topical administration to a subject. Such topical formulations are particularly useful in the methods of treating, preventing, or alleviating a disease, disorder, or condition. The therapeutic formulation may comprise an appropriate dosage form for topical administration, such as a gel, cream, ointment, salve, or medicated bandage comprising the gel compositions of this disclosure.

Another aspect of this disclosure is a therapeutic formulation comprising the gel composition of this disclosure adapted for rectal administration to a subject. Such rectal formulations are particularly useful in methods of treating, preventing, or alleviating inflammatory bowel diseases, e.g., colitis. The therapeutic formulation may comprise an appropriate dosage form for rectal administration, such as a gel, suspension, or solution comprising the gel compositions of this disclosure.

In further embodiments, the present subject matter relates to a method for treating a gastrointestinal inflammatory disorder, a bowel disease, disorder, or condition in a patient in need thereof, the method comprising topically administering a therapeutically effective amount of a gel composition as described herein to a rectum of the patient. In this regard, the bowel disease, disorder, or condition treatable herein can be selected from the group consisting of inflammatory bowel disease, ulcerative colitis, Crohn's disease, rectal complications, rectal wounds, diabetic ulcers, and any combination thereof. In one embodiment, the bowel disease, disorder, or condition is inflammatory bowel disease. In other embodiments, the bowel disease, disorder, or condition is a gastrointestinal disorder.

Similar to the role of inflammation in slowing or preventing the healing of skin wounds, inflammatory bowel disease (IBD), specifically ulcerative colitis, is characterized by intestinal inflammation, and oxidative stress. Therefore, administration of the gel compositions of this disclosure to target oxidative stress can be used to treat inflammatory bowel diseases by reducing inflammation and oxidative stress in the intestinal mucosa.

The gel compositions of this disclosure may be administered orally or rectally on a chronic or intermittent basis and are suitable for treating, reducing the risk of, preventing, or alleviating a symptom of inflammatory bowel diseases, including ulcerative colitis, indeterminate colitis, and Crohn's disease. In these methods, the response to administration of the gel compositions of this disclosure may include one or more of clinical response, mucosal healing, and remission.

To bring the gel compositions into contact with the inflamed intestinal mucosa, these gel compositions may be formulated for rectal administration, as described above. In these methods, rectal administration of a therapeutic formulation comprising the gel composition of this disclosure may be useful in treating, preventing, or alleviating inflammatory bowel diseases.

In certain embodiments, the topical administration of the gel composition herein provides a reduction in rectal bleeding of the patient.

In further embodiments, the topical administration of the gel composition herein downregulates one or more rectal wound markers selected from the group consisting of VEGF, TNF-alpha, IL-1B, NFkB, STATS, COX2, and IL6.

In these therapeutic methods of this disclosure, the clinician administering treatment will be able to determine the appropriate dose for the individual subject for weight-based or flat dosing (i.e., a particular amount of the gel composition that is administered to every patient regardless of weight). For the prevention or treatment of disease, the appropriate dosage of the gel compositions and any second therapeutic or other compound administered in combination with the gel compositions may depend on the disease state being treated, e.g., the type of wound to be treated or the gastrointestinal inflammatory disorder to be treated (IBD, UC, CD) the severity and course of the disease, whether the gel composition or combination is administered for preventive or therapeutic purposes, previous therapy, the patient's clinical history and response to the gel composition, and the discretion of the clinician. In these methods, the gel compositions can be suitably administered to the patient at one time or more typically over a series of treatments. For example, the gel compositions may be administered once every week, or once every two weeks, or once every four weeks, or once every six weeks, or once every eight weeks for a period of one month (4 weeks), or two months, three months, or six months, or 12 months, or 18 months, or 24 months, or chronically for the lifetime of the patient.

Alternatively, or additionally, the gel composition treatments may be self-administered by the patient. For repeated administrations over several days or longer, depending on the condition, the treatment can be sustained until a desired suppression of disease symptoms occurs. However, other dosage regimens may be useful. Typically, the clinician will administer a gel composition of this disclosure (alone or in combination with a second compound) until a dosage(s) is reached that provides the required biological effect. The progress of the therapy is easily monitored by conventional techniques and assays.

EXAMPLES

Example 1

Preparation of Modified Collagen

A collagen hydrolysates solution was heated to 40-75° C., the pH was adjusted to 5.0-6.5, and papain was added (−.01 to 0,1%) to perform enzymolysis to obtain a first enzymolysis reaction solution.

Example 2

Collagen Characterization

Characterization of collagen used in situ in the present rectal gelling system was performed using a Tube inversion test. Two ml of the date palm extract, vanillic acid, carboxymethyl cellulose, diazepam and stearic acid with the collagen hydrolysates in situ gelling system was transferred into a 5 mL sample tube. The system pH was raised to physiological pH by adding 20μL of 1 M NaOH followed by incubation at 37° C. The hydrogel phase rheology was monitored by inverting the tube at 2 min time interval after incubation. Separately, 2 ml of the gelling system was dialyzed against 1 Phosphate buffer saline pH 7.4 at 37 C for 30 min. The system was monitored every 2 min to observe the gelation.

Example 3

Treatment

Figure 2:
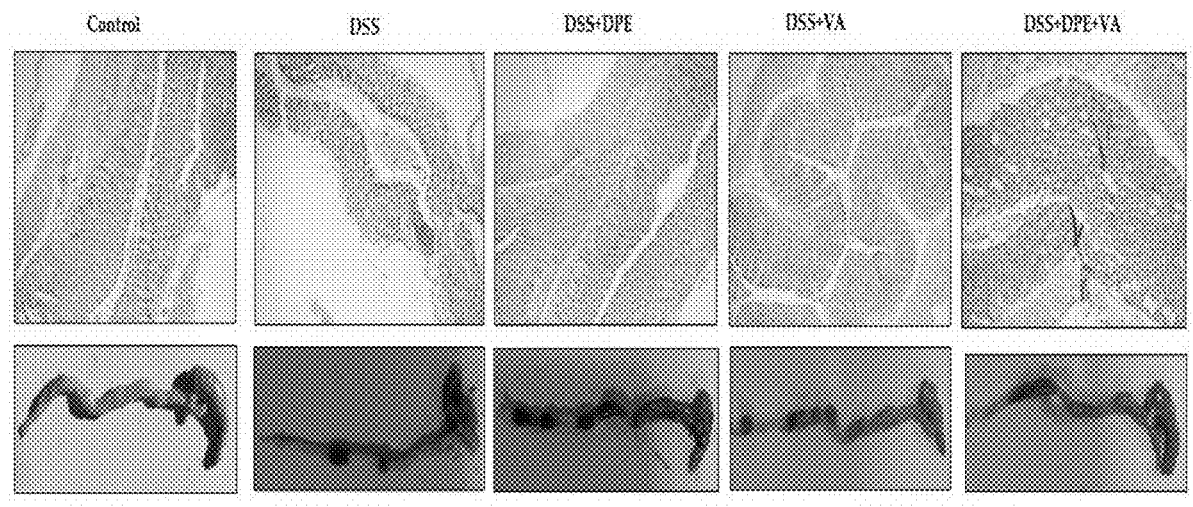
FIG. 2 is a series of micrographs showing histopathological examination of inflammation in the bowels using different compositions.
Figure 3:
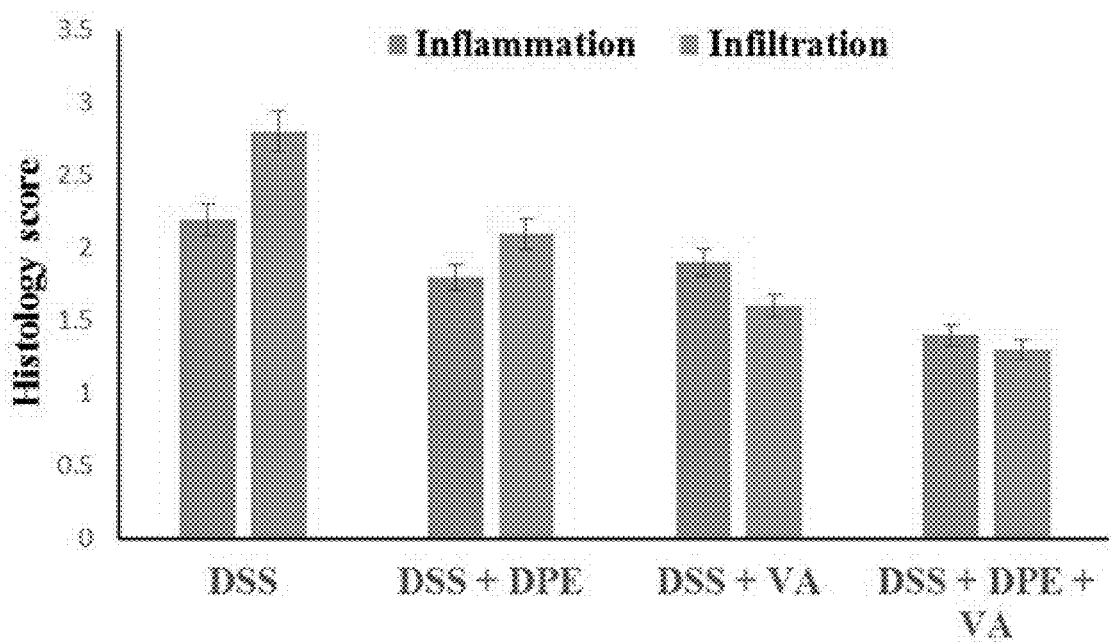
FIG. 3 is a chart showing histopathological scores for inflammation and infiltration in the bowels using different compositions.
Figure 4:
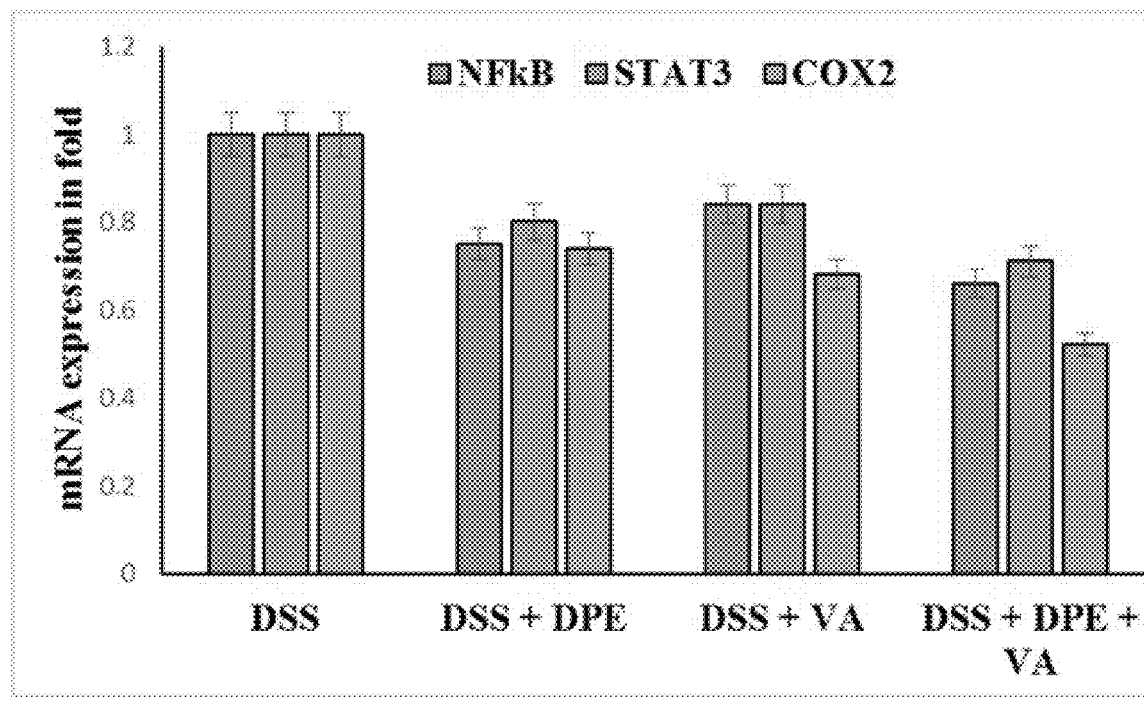
FIG. 4 is a chart showing gene expression of certain inflammatory markers in the bowels following treatment with different compositions.
Figure 5:
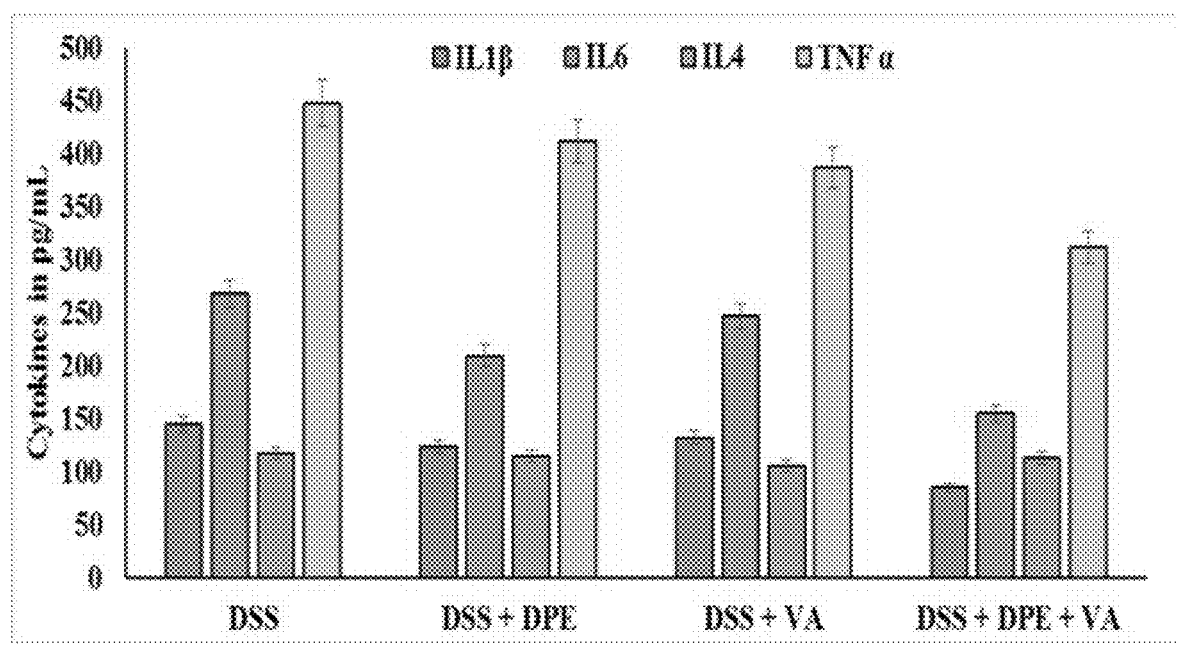
FIG. 5 is a chart showing cytokine estimation in colon tissues following treatment with different compositions.

Collagen (5 to 15 mg/kg b.w), collagen enzymatic hydrolysate (25 to 80 mg/kg b.w), date palm extract suspension (100 to 1000 mg/kg b.w) and vanillic acid (10 to 50 mg/kg b.w) were administered intra rectally from day 6 to 15 into the lumen of the colon of DSS mice. Results of these treatments can be seen in FIGS. 1-5.

Specifically, the present compositions provided higher clinical effectiveness in treatment of immunological mediated inflammatory bowel diseases of the intestinal-digestive tract, reduced disease symptoms and treatment period. The clinical assessment on day 10 of rectal injury using dextran sulfate sodium/TNBS and acetic acid revealed that both the modified collagen 0.1 to 2% complexed with vanillic acid, date phenols and chitosan demonstrated significant reduction in the rectal bleeding compared to reference mesalamine treatment. The rectal wound markers VEGF, TNF-alpha, IL-1B and IL6 were downregulated in the injured tissues. Collagen complex treatments showed significant reduction in mucosal damage score and facilitated faster regeneration of damaged mucosa.

It is to be understood that the gel composition is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for treating a bowel disease, disorder, or condition in a patient in need thereof, the method comprising:
topically administering a therapeutically effective amount of a gel composition to a rectum of the patient;
the gel composition comprising:
about 0.1 to about 2.5 wt. % of an anti-epileptic agent;
about 0.8 to about 2.0% wt. % of a collagen complexed with a date palm extract of Khalas cultivar and carboxymethylcellulose;
including about 10 to about 50 μg/mL of vanillic acid;
about 0.1 to about 0.3 μg of stearic acid; and
water;
wherein all wt. % are based on g/100 g of the gel composition;
wherein the bowel disease, disorder, or condition is selected from the group consisting of rectal complications, rectal wounds, and a combination thereof.

2. The method of claim 1, wherein the topical administration of the gel composition provides a reduction in rectal bleeding of the patient.

3. The method of claim 1, wherein the topical administration of the gel composition downregulates one or more rectal wound markers selected from the group consisting of VEGF, TNF-alpha, IL-1B, NFkB, STATS, COX2, and IL6.

4. The method of claim 1, the gel composition further comprising one or more selected from the group consisting of chitosan, timogen, propylene glycol, Carbopol, EDTA, and sodium hydroxide.

5. The method of claim 1, wherein the collagen is pepsin treated collagen I.

6. The method of claim 1, wherein the collagen includes collagen enzymatic hydrolysates.

7. The method of claim 1, wherein the date palm extract includes phenolics in addition to vanillic acid.

8. The method of claim 1, the gel composition further comprising about 0.25 to about 1.5 wt. % of the anti-epileptic agent.

9. The method of claim 1, the gel composition further comprising about 0.75 wt. % of the anti-epileptic agent.

10. The method of claim 1, wherein the anti-epileptic agent is a phenobarbital.

11. The method of claim 10, wherein the phenobarbital is diazepam.

12. The method of claim 1, wherein the gel composition is formulated for topical administration.

\* \* \* \* \*